US006271417B1

(12) United States Patent
Focht et al.

(10) Patent No.: US 6,271,417 B1
(45) Date of Patent: Aug. 7, 2001

(54) PROCESS FOR PRODUCING 3-BROMOBENZOYL HALIDES

(75) Inventors: Gary D. Focht; W. Dirk Klobucar, both of Baton Rouge, LA (US)

(73) Assignee: Albemarble Corporation, Richmond, VA (US)

(*) Notice: Subject to any disclaimer, the term of this patent is extended or adjusted under 35 U.S.C. 154(b) by 0 days.

(21) Appl. No.: 09/406,246

(22) Filed: Sep. 24, 1999

Related U.S. Application Data

(63) Continuation-in-part of application No. 09/111,935, filed on Jul. 8, 1998, now Pat. No. 6,096,920.

(51) Int. Cl.[7] .................................................. C07C 51/58
(52) U.S. Cl. ................................................................ 562/840
(58) Field of Search .............................................. 562/840

(56) References Cited

U.S. PATENT DOCUMENTS

| | | |
|---|---|---|
| 2,019,015 | 10/1935 | McCullough . |
| 2,607,802 | 8/1952 | Britton et al. . |
| 4,190,600 | * 2/1980 | Landauer . |
| 4,983,781 | 1/1991 | Desmurs et al. . |
| 5,107,044 | 4/1992 | Nonn . |

FOREIGN PATENT DOCUMENTS

| | | |
|---|---|---|
| 1933486 | 1/1971 | (DE) . |
| 2144259 | 3/1972 | (DE) . |
| 2950877 | 6/1981 | (DE) . |

OTHER PUBLICATIONS

Olah et al., "Aromatic Substitution. XIV. Ferric Chloride Catalyzed Bromination of Benzene and Alkylbenzenes With Bromine in Nitromethane Solution", Journal Am. Chem. Soc., 1964, vol. 86, Issue 6, pp. 1039–1044.

Olah et al., "Aromatic Substitution. XV. Ferric Chloride Catalyzed Bromination of Halobenzenes in Nitromethane Solution", Journal Am. Chem. Soc., 1964, vol. 86, Issue 6, pp. 1044–1046.

Olah et al., "Aromatic Substitution. XVI. Freidel–Crafts Isopropylation of Benzene and Methylbenzenes with Isopropyl Bromide and Proplyene" Journal Am. Chem. Soc., 1964, vol. 86, Issue 6, pp. 1046–1054.

Caplus Abstract, DE 1933486, 1971.
Caplus Abstract, DE 21144259, 1972.
Caplus Abstract, DE 2950877, 1981.

* cited by examiner

*Primary Examiner*—Paul J. Killos
(74) *Attorney, Agent, or Firm*—Philip M. Pippenger

(57) ABSTRACT

Meta-bromination with suppression of para-bromination is achieved by forming a reaction mixture comprised of (i) bromine chloride, (ii) a bromination catalyst, and (iii) a benzoyl halide, and maintaining the temperature of the resultant reaction mixture at one or more temperatures above 0° C., but not greater than 30° C. The bromine chloride is preferably formed in situ, most preferably by sparging gaseous chlorine into a mixture of bromine, finely-divided iron, and benzoyl chloride.

16 Claims, No Drawings

PROCESS FOR PRODUCING 3-BROMOBENZOYL HALIDES

REFERENCE TO RELATED APPLICATIONS

This application is a continuation-in-part of a commonly-owned U.S. application Ser. No. 09/111,935, filed Jul. 8, 1998, now U.S. Pat. No. 5,096,920.

TECHNICAL FIELD

This invention relates to a novel and efficient method for the meta-bromination of benzoyl halides.

BACKGROUND

Meta-bromination reactions of benzoyl halides are integral reactions in the production of a variety of widely used pharmaceutical compounds, and as such, they are reactions of considerable commercial importance. As an example of the utility of this reaction, it can be used to prepare meta-bromobenzoyl chloride, which is an intermediate in the production of ketoprofen drugs, a commonly-prescribed class of pain relievers.

It has long been known that bromine chloride is an effective bromination agent for a diverse group of aromatic substrates. In addition to brominating benzoyl halides, it has also been used to brominate toluene, anisole, substituted biphenyl compounds, and other aromatic compounds. In the case of benzoyl halides, metabromination with bromine chloride is more effective than with bromine itself, and is thus deemed particularly advantageous.

However, the preparation and procurement of bromine chloride can be difficult in that bromine chloride is quite unstable. Once prepared, it readily decomposes into bromine and chlorine, even at relatively low temperatures, such as room temperature. Because of this characteristic, when brominating at temperatures which are higher than room temperature, it is often necessary to supply bromine chloride to the reaction at a relatively high rate in order to have sufficient bromine chloride in the reaction mixture to obtain effective bromination, and much bromine chloride is often wasted in the process.

In spite of the above-described difficulties, metabromination of benzoyl halides with bromine chloride is still performed at temperatures which are significantly higher than room temperature. There are several reasons for such a practice.

First, attempts to brominate a benzoyl halide at low temperatures can be problematic. Unlike processes for the bromine chloride bromination of other aromatic compounds, such as toluene and anisole, which proceed readily at temperatures of about 0° C. and below, the metabromination reaction of benzoyl halides with bromine chloride can be impeded by such temperatures yielding significantly less metabrominated product than can be achieved at higher temperatures.

In addition, the use of high temperatures in the bromination of benzoyl bromides with bromine chloride has a basis in the teachings of elementary organic chemistry coupled with the experience gained in brominating other aromatic compounds. Without desiring to be bound by theory, the relationship between ring bromination rate and reaction temperature can be understood in light of the following reasoning. It has been observed that substituents on the aromatic ring which are "electron-donating" also generally engender ease of bromination at low temperatures. Such an effect can be explained by the logical conclusion that these substituents readily increase the electron density on the aromatic ring via an "electron-donating" effect. Such increased electron density facilitates the electrophilic addition of bromine. Accordingly, compounds such as toluene, anisole and others which bear "electron-donating" substituents on the aromatic ring, should require only moderate temperatures in order to undergo efficient bromination. By further application of this reasoning, the bromination of benzoyl halides, as well the bromination of other aromatic compounds which similarly bear "electron-withdrawing" substituents on their aromatic rings, should require higher temperatures in order to undergo efficient bromination (see, for example, U.S. Pat. No. 2,607,802 to Britton et al.). Hence the use of high temperatures.

In addition to the decomposition of bromine chloride at reaction temperatures often used in the bromination of benzoyl halides with bromine chloride, a second problem encountered in the fore-mentioned bromination reaction is the concomitant formation of p-bromobenzoyl halide. For example, known methods for the bromine chloride metabromination of benzoyl chloride often yield as much as approximately two percent p-bromobenzoyl chloride. The competitive side reaction which produces the para-isomer also diminishes the purity and yield of the metabrominated product. The presence of the para-isomer has yet another undesirable consequence in that its removal from the meta-isomer is particularly difficult since the similarity in boiling points of the isomers can limit the effectiveness of conventional separation methods such as distillation.

A process for the bromine chloride metabromination of benzoyl chloride which surmounts the problem of bromine chloride instability at high temperatures, which forms parabromobenzoyl chloride in lower weight percent than obtained in currently-practiced processes, and yet proceeds with a reaction rate similar to that observed with bromine chloride at high temperatures would represent a significant improvement in the state of the art.

SUMMARY OF THE INVENTION

A process has been found for the metabromination of benzoyl halides which avoids the handling of bromine chloride at high temperatures, yields parabromobenzoyl halide in weight percent amounts which are below those of currently-practiced processes, and yet has a reaction rate which is comparable to that of currently-practiced processes. It has been discovered that when the bromine chloride metabromination of benzoyl chloride is carried out at temperatures above 0° C., but below 30° C., the reaction rate remains comparable to that obtained at 80° C., rather than monotonically decreasing with temperature. Such behavior is in surprising contrast to the sluggish reaction rates which are observed when the reaction is carried out at temperatures of 0° C. and below.

Accordingly, an embodiment of the process of this invention is a process which comprises A) forming a reaction mixture comprised of (i) bromine chloride, (ii) a bromination catalyst, and (iii) a benzoyl halide; and
B) maintaining the reaction mixture of A) at one or more temperatures above 0° C., but not greater than 30° C., such that a metabromobenzoyl halide is formed.

If desired, the bromine chloride of A) above can be formed in a separate reaction vessel prior to its introduction to the reaction mixture, by such a method as combining chlorine and bromine in a suitable solvent such as to effect the formation of bromine chloride. It is also within the scope of this invention to form the bromine chloride within the reaction mixture itself, i.e., in situ. One way of forming bromine chloride in the reaction mixture is to combine bromine and chlorine in the reaction mixture in a one-to-one molar ratio. However, it is particularly convenient to introduce bromine to the reaction mixture in the absence of chlorine, and subsequently contact gaseous chlorine with the bromine-containing reaction mixture. Thus, a preferred embodiment of the process of this invention is a process which comprises A) forming a reaction mixture comprised of (i) bromine chloride, (ii) a bromination catalyst, and (iii) a benzoyl halide; and B) maintaining the reaction mixture of A) at one or more temperatures above 0° C., but not greater than 30° C., such that a metabromobenzoyl halide is formed, wherein the reaction mixture of A) is formed by 1) forming a prior mixture comprised of (a) bromine, (b) a bromination catalyst and (c) benzoyl halide; and 2) contacting such prior mixture with gaseous chlorine.

It can be most convenient to introduce the gaseous chlorine into the bromine-containing prior mixture by sparging it into the mixture. By sparging is meant introducing gaseous chlorine directly into the bromine-containing prior mixture, typically at a position below the surface of the liquid phase of the prior mixture, such that the chlorine moves or is moved about in the prior mixture, thus resulting in the formation of bromine chloride.

A number of bromination catalysts have been used with bromine chloride in order to promote the bromination of aromatic compounds. However, a bromination catalyst formed in situ from finely divided iron and bromine is particularly convenient and effective in this capacity, especially when utilized with the in situ formation of bromine chloride. In this embodiment, it is preferable to use finely divided iron in the formation of a bromine-containing prior mixture. Thus, another preferred embodiment of the process of this invention is a process which comprises A) forming a reaction mixture comprised of (i) bromine chloride, (ii) finely divided iron, and (iii) a benzoyl halide; and B) maintaining the reaction mixture of A) at one or more temperatures above 0° C., but not greater than 30° C., such that metabromobenzoyl chloride is formed, wherein the reaction mixture of A) is formed by 1) forming a prior mixture comprised of (a) bromine, (b) finely divided iron and (c) a benzoyl halide; and 2) contacting such prior mixture with gaseous chlorine.

It is most preferable to perform this embodiment by sparging the gaseous chlorine gas of 2) through the prior mixture of 1) such as to effect the formation of bromine chloride.

The above and other embodiments will be apparent from the ensuing description and appended claims.

FURTHER DESCRIPTION OF THE INVENTION

Typically, benzoyl chloride and benzoyl bromide are preferred substrates in the bromination reaction. It is most preferred to use benzoyl chloride as the substrate. Benzoyl halides are readily available, and can be easily obtained from chemical supply houses such as Aldrich Chemical Company in Milwaukee, Wisconsin, or Alfa Aesar Organics in Ward Hill, Mass.

The bromination reagent, bromine chloride is easily prepared by such a method as simultaneous introduction of liquid bromine and chlorine gas into a solvent which is inert to bromine and chlorine, such as carbon tetrachloride. For example, bromine liquid can be added to a solvent which is inert to bromination into which chlorine is simultaneously bubbled. In accordance with a preferred embodiment of this invention disclosed above, chlorine gas is sparged through a bromine containing mixture. It is possible to omit the solvent entirely by cooling a portion of bromine in a vessel to a temperature below 10° C. and subsequently adding chlorine gas.

In general, when forming bromine chloride from bromine and chlorine, it is desirable to maintain the halogen reactants at a temperature below about 10° C. in order to reduce the tendency for the nascent bromine chloride to decompose into bromine and chlorine gas. Such temperature precautions are particularly important if the bromine chloride is not immediately reacted with the benzoyl halide substrate, i.e. stored or allowed to stand for a period of time.

In performing the process of the invention, the proportion of bromine chloride to benzoyl halide is not critical to the realization of para isomer repression. Preferably, the mole ratio of bromine chloride to benzoyl halide is in the range of from about 0.8 to about 1.3 moles of bromine chloride per mole of benzoyl halide. It is more preferable to have a mole ratio of bromine chloride to benzoyl chloride in the range of about 0.9 to about 1.2 moles of bromine chloride per mole of benzoyl chloride. Most preferable is a ratio of about 1.1 moles of bromine chloride per mole of benzoyl chloride.

It is highly advantageous to conduct the bromination reaction at one or more temperatures above 0° C., but not greater than 30° C. A more preferred temperature range in which to conduct the bromination reaction is from about 5° C. to about 25° C. The most preferred temperature range is from about 7° C. to about 15° C. It is permissible for the reaction temperature to rise somewhat above or to fall somewhat below the temperature ranges elucidated provided that during at least a major portion (i.e., greater than 50%) and preferably in the range of about 70 to 100% of the total bromination reaction period, the foregoing temperature conditions are maintained in the reaction mixture.

As bromine chloride tends to decompose at pressures which are less than atmospheric, it is recommended that the process of this invention be conducted at pressures which are least atmospheric. Pressures which are greater than atmospheric are permissible as long as the bromination reaction is not severely impeded. It is desirable to conduct the bromination process, as well as the in situ formation of bromine chloride, if applicable, at a pressure in the range of from about 0 psig to about 10 psig. A pressure of about 3 psig is most desirable.

The process of this invention can be conducted in the presence of an ancillary solvent. If such a solvent is used, it is highly advantageous that it be inert to reaction with bromine or chlorine under the reaction conditions of the bromination. It is advisable that such a solvent also be inert to other interactions which would impair the high meta isomer selectivity of the inventive process. Examples of such interactions include, but are not limited to, interaction with benzoyl chloride and complexation with the bromination catalyst. Non-limiting examples of such solvents are carbon tetrachloride, dichloromethane, chlorobenzene, bromochloromethane, dibromomethane, ethylene dichloride, and similar solvents.

A wide variety of bromination catalysts can be used in the conduction of the inventive bromination process described herein. Typically, Lewis acids are efficient bromination catalysts, and strong Lewis acids catalyze the bromination reaction more effectively than weak Lewis acids. It is, however, preferable to employ a catalyst which is non-oxygen-coordinating, as catalysts which are oxygen-coordinating, such as aluminum, tend to complex with the benzoyl halide and impair the efficiency of the bromination reaction. Examples of suitable catalysts are ferric chloride ($FeCl_3$), ferric bromide ($FeBr_3$), stannic chloride ($SnCl_4$), stannous chloride ($SnCl_2$) and antimony pentafluoride ($SbCl_5$).

The catalyst is used in amounts such as to effect efficient bromination of the benzoyl halide. This amount can vary with the particular catalyst employed, but it is preferably in the range of from about 0.1 to about 0.001 moles of catalyst per mole of benzoyl halide. It is more preferable to use the catalyst in an amount which is in the range of from about 0.05 to about 0.005 moles of catalyst per mole of benzoyl halide.

In general, the catalyst can exist in the reaction mixture as a solid or a liquid, or it can be dissolved or finely dispersed throughout the reaction mixture. If desired, a solid catalyst can be supported by means of a refractory support, or it can be contained in a fixed or fluidized bed.

In one mode of catalyst preparation, the catalyst can be formed in the reaction mixture, i.e., in situ. This is accomplished by using finely divided iron in addition to, or instead of, using a preformed bromination catalyst. Without desiring to be bound by theory, it is believed that after the introduction of bromine and/or chlorine, iron bromide and/or iron chloride are formed in the reaction mixture, and these compounds subsequently act to catalyze the bromination reaction.

The bromination process described herein can be implemented as a batch, semicontinuous or continuous process, as deemed convenient for the particular application. If the reactants (i.e. benzoyl halide and bromine) are to be flowed past the catalyst and a high degree of metabromobenzoyl halide formation is desired, it is advisable to ensure that the reactants are in the presence of the catalyst for a time sufficient for such conversion.

In general, the reaction mixture can be formed in many ways. Although it is preferable to combine the benzoyl chloride and the bromination catalyst, and subsequently introduce the bromine chloride, it is permissible to add the bromination catalyst to a preformed mixture of the benzoyl chloride and the bromine chloride. Alternatively, the benzoyl chloride can be added to a preformed mixture of the bromine chloride and the bromination catalyst.

If the bromine chloride is formed in situ from bromine and chlorine, it is permissible to add the reaction mixture components in any order, with the provision that it is not advisable to combine the benzoyl chloride and the chlorine with out the presence of bromine in the reaction mixture.

In yet another preferred embodiment, described heretofore, wherein finely divided iron is present in the reaction mixture and chlorine gas is subsequently sparged through the mixture, the reaction mixture can be formed by adding the components in any order, with the provision that neither the bromine nor the iron are added last.

The atmosphere under which the bromination reaction takes place is preferably anhydrous. In the presence of water, the formation of benzoic acid from benzoyl halide has been observed. The use of an anhydrous atmosphere of inert gas such as anhydrous nitrogen or argon is not necessary, however, as the process can be successfully conducted in the presence of anhydrous gases such as carbon dioxide, as well as in the presence of anhydrous mixtures, such as dry air.

It is not necessary to mechanically agitate the reaction mixture in order to realize the benefits of this invention, however, especially when gaseous chlorine is being sparged into the reaction mixture. However, the use of mechanical agitation can be desirable in ensuring intimate contact between the reactants. Also use mechanical agitation may result in increased reaction, especially at low temperatures. Thus, a mechanical stirrer, a shaker, a rocking autoclave or other means for providing agitation can be utilized when conducting the process of this invention.

Another beneficial feature of this reaction is the appreciable rate at which the metabromobenzoyl halide can be obtained, even at temperatures as low as about 5° C. At temperatures of approximately 0° C. and below, the reaction rate can decrease sharply as temperature is decreased.

In order to obtain a high level of reaction completion, it is advisable to allow the reaction to proceed in an uninterrupted manner for a period of time following the addition of bromine chloride. Such a maturation time is advisable even if the bromine chloride has been formed in situ. In the case of in situ bromine chloride formation, it is recommended that the maturation time begin after the addition of all bromine chloride-forming elements to the reaction mixture (e.g., bromine and chlorine). Preferably, the maturation time is at least about 1 hour. More preferably, the maturation time is at least 3 hours.

If the bromine chloride is to be formed in situ, the preferred method for such formation is introduce chlorine gas into a mixture of bromine, benzoyl halide and bromination catalyst and/or finely-divided iron, preferably by sparging the chlorine gas through the bromine-containing mixture. Typically the temperature of the mixture bromine, benzoyl halide and bromination catalyst and/or finely-divided iron is reduced to below room temperature before the feed of the chlorine is initiated.

As the metabromination reaction is an exothermic reaction, the chlorine should be fed into the reaction mixture at a rate such that the temperature of the reaction mixture does not rise to temperatures in excess of 30° C. Thus, if, for a given rate of chlorine addition, the reaction mixture tends toward temperatures in excess of 30° C., the rate of chlorine addition can be decreased to bring the temperature back into the desired temperature range. Conversely, if the temperature of the reaction mixture is undesirably low, an increase in the rate of addition of chlorine gas can be employed to raise the temperature of the reaction mixture. On completion of the bromination it is desirable to sparge the reaction mass with nitrogen to remove bromine, hydrogen chloride, and hydrogen bromide from the reaction mass. The temperature of the reaction mass can be suitably elevated during the sparging with nitrogen, and thus the reaction mass can be warmed by application of heat before and during the sparging, if desired.

Comparative Examples A to E demonstrate disadvantages of conducting the bromination reaction under conditions not in accordance with this invention, such as in Britton et al. U.S. Pat. No. 2,607,802.

COMPARATIVE EXAMPLE A

Preparation of Metabromobenzoyl Chloride (MBBC) by the Procedure of U.S. Pat. No. 2,607, 802

To a half jacketed 2 liter flask with a flush bottom stopcock and equipped with a dry ice condenser was added 702 g of benzoyl chloride (4.99 mol) and 1207 g bromine (7.55 mol). The contents of the flask were stirred and cooled to 0° C. under a nitrogen blanket and then chlorine (535 g, 7.66 mol) was added from a gas cylinder on a scale over 0.9 hours at −1 to −7° C. A 3-L four necked flask in a heating mantle equipped with a reflux condenser (cooled at −15° C.), mechanical stirrer, thermocouple well and a jacketed 500 ml addition flask cooled to −25° C. was used for the bromination reaction. The above 2 liter flask which was also cooled to −25° C. was mounted above the addition funnel and was connected to it with Teflon tubing so that the funnel could be refilled. To the 3-L flask containing 1399 g benzoyl chloride (9.95 mol) and 24.9 g of ferric chloride was added the mixture from the 2 liter over 7.9 hours at 75 to 87° C. The reaction mixture was stirred for 1 hour at 80° C. and then allowed to stand and cool overnight. The reaction mixture was warmed at RT-55° C. while sparged with nitrogen for 3 hours. There was obtained 3258 g of crude product which contained 0.34 wt % residual bromine. By GC area % the material contained 7.1% benzoyl chloride, 3.6% chlorobenzoyl chlorides, 78.2% metabromobenzoyl chloride, 1.3% parabromobenzoyl chloride, and 2.4% dibromobenzoyl chlorides.

COMPARATIVE EXAMPLE B

Bromination with BrCl at about 80° C.

To a jacketed 500 ml 4 necked flask with a bottom stopcock equipped with a mechanical stirrer, thermocouple well, a dry ice condenser and a chlorine feed tube was added 141.5 benzoyl chloride (1.01 mol) and 240 g of bromine (1.50 mol). The stirred mixture was cooled and 107.8 g chlorine (1.52 mol) was added over 0.5 hr at −1.5 to −5.4° C.

To a 1-L four necked flask in a heating mantle equipped with a condenser and a 500 ml jacketed addition funnel was added 5.02 g of $FeCl_3$ (0.031 mol) and 279.7 g of benzoyl chloride (total of 421.2 g or 3.00 mol). The bromine chloride/benzoyl chloride solution was transferred to the addition funnel which was cooled at −10° C. The bottom flask was warmed to 83° C. and the contents of the addition funnel were added over a period of 5.5 hours at 83 to 91° C. The reaction mixture was stirred for 0.4 hr at 40° C. and then sparged with nitrogen for 1.2 hrs at 40–49° C. There was obtained 648 g of dark crude product. By GC area % the material contained 9.1% benzoyl chloride, 3.4% chlorobenzoyl chlorides, 81.9% metabromobenzoyl chloride, 1.4% parabromobenzoyl chloride, and 4.2% dibromobenzoyl chlorides.

COMPARATIVE EXAMPLE C

Bromination with BrCl at about 40° C.

To a jacketed 500 ml 4 necked flask with a bottom stopcock equipped with a mechanical stirrer, thermocouple well, a dry ice condenser and a chlorine feed tube was added 142 benzoyl chloride (1.01 mol) and 240 g of bromine (1.50 mol). The stirred mixture was cooled to −9.5° C. and 107 g chlorine (1.51 mol) was added over 1.1 hr at −8.2 to −9.5° C.

To a 1-L four necked flask in a heating mantle equipped with a condenser and a 500 ml jacketed addition funnel was added 5.02 g of $FeCl_3$ (0.031 mol) and 281 g of benzoyl chloride (total of 423 g or 3.01 mol). The bromine chloride/benzoyl chloride solution was transferred to the addition funnel which was cooled at −10° C. The bottom flask was warmed to 40° C. and the contents of the addition funnel were added over a period of 4 hours at 38 to 40° C. The reaction mixture was stirred for 0.4 hr at 40° C. and then sparged with nitrogen for 1.2 hrs at 40° C. There was obtained 648 g of dark crude product. By GC area % the material contained 9.5% benzoyl chloride, 5.1% chlorobenzoyl chlorides, 76.9% metabromobenzoyl chloride, 0.8% parabromobenzoyl chloride, 0.4% orthobromobenzoyl chloride, 1.6% chlorobromobenzoyl chlorides, and 4.1% dibromobenzoyl chlorides.

COMPARATIVE EXAMPLE D

Bromination of Benzoyl Chloride with BrCl Generated In-situ at about −4° C.

A jacketed 1L 4 necked round bottom flask with a bottom stopcock, a mechanical stirrer, a chlorine inlet tube (0.25" o.d. tubing extending to just above the agitator blade), a thermocouple well, a Friedrich condenser (tap water for cooling) with a nitrogen line "T"eed into the top of the condenser and a caustic scrubber was used for the reaction. To the 1L pot was added 421.4 g of benzoyl chloride (3.00 mol), 4.2 g iron powder (0.075 g-atom), and 266 g bromine (1.66 mol). The reaction mixture was cooled to 1.2° C. and then the $Cl_2$ feed was started. Over a 4.3 hour period, chlorine (117 g, 1.65 mol) was added to the solution (below the surface of the solution) while stirred at 2 to −5° C. (the caustic trap had gained about 85 g during the reaction). The reaction mixture was stirred for 1.4 hour at −5° C. (the caustic trap had gained 98.4 g total at this point). It was then warmed to about 50° C. while sparging the solution with nitrogen for about 17 hours to remove the bromine, hydrogen chloride and hydrogen bromide. There was obtained 628 g of greenish-black liquid MBBC which contained some iron powder. Some iron powder remained in the bottom of the flask. The sample residual bromine level was found to be 0.01 wt %. By GC area % the material contained 17.2% benzoyl chloride, 3.2% chlorobenzoyl chlorides, 70.9% metabromobenzoyl chloride, 0.3% parabromobenzoyl chloride, 0.3% orthobromobenzoyl chloride, 0.4% chlorobromobenzoyl chlorides, and 1.8% dibromobenzoyl chlorides.

COMPARATIVE EXAMPLE E

Bromination of Benzoyl Chloride with BrCl Generated In-situ at Temperatures Between 0° C. an −10° C.

A jacketed 1L 4 necked round bottom flask with a bottom stopcock, a mechanical stirrer, a chlorine inlet tube (0.25" o.d. tubing extending to just above the agitator blade), a thermocouple well, a Friedrich condenser (tap water for cooling) with a nitrogen line "T"eed into the top of the condenser and a caustic scrubber was used for the reaction. To the 1L pot was added 421.3 g of benzoyl chloride (3.00 mol), 2.13 g iron powder (0.038 g-atom), and 251.7 g bromine (1.57 mol). The reaction mixture was cooled to 4.6° C. and then the $Cl_2$ feed was started. Over a 5.5 hour period, chlorine (117 g, 1.65 mol) was added to the solution (below the surface of the solution) while stirred at temperatures in the range of from about 0° C. to about −10° C. (mostly at about −8° C., the caustic trap had gained about 57 g during the reaction). The reaction mixture was stirred for 16.5 hour at −10° C. (the caustic trap had gained 72 g total at this point). It was then gradually warmed to about 30° C. over a 3 hour period (the caustic trap had gained a total of 78.5 g). The reaction mixture was stirred at 30° C. while sparging the solution with nitrogen for about 20 hours to remove the bromine, hydrogen chloride and hydrogen bromide. There was obtained 625 g of greenish-black liquid MBBC which contained some iron powder. Some iron powder remained in the bottom of the flask. The sample residual bromine level was found to be 0.01 wt %. By GC area % the material contained 22.7% benzoyl chloride, 2.9% chlorobenzoyl chlorides, 70.0% metabromobenzoyl chloride, 0.3% parabromobenzoyl chloride, 0.4% orthobromobenzoyl chloride, 0.3% chlorobromobenzoyl chlorides, and 1.6% dibromobenzoyl chlorides.

The following Examples illustrate the practice and advantages of this invention. These Examples are not intended to limit, and should not be construed as limiting, the scope of this invention to the details set forth therein.

EXAMPLE 1

Bromination of Benzoyl Chloride with BrCl Generated In-situ at about 5° C.

A jacketed 1L 4 necked round bottom flask with a bottom stopcock, a mechanical stirrer, a chlorine inlet tube (0.25" o.d. tubing extending to just above the agitator blade), a thermocouple well, a Friedrich condenser (tap water for cooling) with a nitrogen line "T"eed into the top of the condenser and a caustic scrubber was used for the reaction. To the 1L pot was added 422 g of benzoyl chloride (3.00 mol), 1.7 g iron powder (0.030 g-atom), and 312 g bromine (1.95 mol). The reaction mixture was cooled to 2.6° C. and then the $Cl_2$ feed was started. Over a 4.4 hour period, chlorine (138 g, 1.95 mol) was added to the solution (below the surface of the solution) while stirred at 2.6 to 7.1° C. (the caustic trap had gained about 106 g during the reaction). The reaction mixture was stirred for 1.0 hour at 5° C. (the caustic trap had gained 115 g total at this point). It was then warmed to about 48° C. while sparging the solution with nitrogen for about 16 hours to remove the bromine, hydrogen chloride and hydrogen bromide. There was obtained 647 g of greenish-black liquid MBBC which contained some iron powder. Some iron powder remained in the bottom of the flask. The sample residual bromine level was found to be 0.07 wt %. By GC area % the material contained 8.2% benzoyl chloride, 3.5% chlorobenzoyl chlorides, 73.7% metabromobenzoyl chloride, 0.5% parabromobenzoyl chloride, 0.3% orthobromobenzoyl chloride, 0.3% chlorobromobenzoyl chlorides, and 1.9% dibromobenzoyl chlorides.

EXAMPLE 2

Bromination of Benzoyl Chloride with BrCl Generated In-situ at about 10° C.

A jacketed 1L 4 necked round bottom flask with a bottom stopcock, a mechanical stirrer, a chlorine inlet tube (0.25" o.d. tubing extending to just above the agitator blade), a thermocouple well, a Friedrich condenser (tap water for cooling) with a nitrogen line "T"eed into the top of the condenser and a caustic scrubber was used for the reaction. To the 1L pot was added 421.5 g of benzoyl chloride (3.00 mol), 2.1 g iron powder (0.038 g-atom), and 276 g bromine (1.73 mol). The reaction mixture was cooled to 10.9° C. and then the $Cl_2$ feed was started. Over a 4.3 hour period, chlorine (125 g, 1.76 mol) was added to the solution (below the surface of the solution) while stirred at 8.7 to 11.0° C. (the caustic trap had gained about 108.8 g during the reaction). The reaction mixture was stirred for 0.9 hour at 8 to 10° C. (the caustic trap had gained 115 g total at this point). It was then warmed to about 47° C. while sparging the solution with nitrogen for about 16.5 hours to remove the bromine, hydrogen chloride and hydrogen bromide. There was obtained 655 g of greenish-black liquid MBBC which contained some iron powder. Some iron powder remained in the bottom of the flask. The sample residual bromine level was found to be 0.21 wt %. By GC area % the material contained 7.6% benzoyl chloride, 3.8% chlorobenzoyl chlorides, 80.1% metabromobenzoyl chloride, 0.5% parabromobenzoyl chloride, 0.3% orthobromobenzoyl chloride, 0.8% chlorobromobenzoyl chlorides, and 3.3% dibromobenzoyl chlorides.

EXAMPLE 3

Bromination of Benzoyl Chloride with BrCl Generated In-situ at Temperatures Between 4° C. and 9° C.

A jacketed 12L 4 necked round bottom flask with a bottom stopcock, a mechanical stirrer, a chlorine inlet tube (0.25" o.d. tubing extending to just above the agitator blade), a thermocouple well, a Friedrich condenser (tap water for cooling) with a nitrogen line "T"eed into the top of the condenser and a caustic scrubber was used for the reaction. To the 1L pot was added 8853 g of benzoyl chloride (62.77 mol), 45.8 g iron powder (0.82 g-atom), and 5282 g bromine (65.9 mol). The reaction mixture was cooled to 9° C. and then the $Cl_2$ feed was started. Over a 11 hour period, chlorine (2352 g, 33.2 mol) was added to the solution (below the surface of the solution) while stirred at temperatures in the range of from about 4 to about 9° C. (mostly at about 5 to 7° C.). The reaction mixture was stirred for 0.6 hour at 5 to 12° C. The reaction mixture was stirred at 23° C. while sparging the solution with nitrogen for about 11 hours to remove the bromine, hydrogen chloride and hydrogen bromide. There was obtained 13758 g of greenish-black liquid MBBC which contained some iron powder. Some iron powder remained in the bottom of the flask. The sample residual bromine level was found to be 0.35 wt %. By GC area % the material contained 8.6% benzoyl chloride, 3.5% chlorobenzoyl chlorides, 78.2% metabromobenzoyl chloride, 0.5% parabromobenzoyl chloride, 0.1% orthobromobenzoyl chloride, 0.8% chlorobromobenzoyl chlorides, and 3.3% dibromobenzoyl chlorides.

It is to be understood that the reactants and components referred to by chemical name or by formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or re-actions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient just as it existed at the time just before it was first contacted, blended or mixed with one or more other substances, components and/or ingredients in accordance with the present disclosure. Thus the fact that a substance, component or ingredient may have lost its original identity through a chemical reaction or transformation through the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process which comprises
    A) forming a reaction mixture comprised of (i) bromine chloride, (ii) a bromination catalyst, and (iii) a benzoyl halide; and
    B) maintaining the reaction mixture of A) at one or more temperatures above 0° C., but not greater than 30° C., such that meta-bromobenzoyl halide is formed.

2. A process as in claim 1 wherein bromine chloride in the reaction mixture of A) is formed in situ.

3. A process as in claim 1 wherein bromine chloride is formed in the reaction mixture of A) by introducing gaseous chlorine into a mixture initially comprised of bromine, a bromination catalyst, and a benzoyl halide, so that at least a portion of the bromine and at least a portion of the chlorine react to produce bromine chloride in situ.

4. A process as in claim 3 wherein the chlorine is sparged through the mixture initially comprised of bromine, a bromination catalyst, and a benzoyl halide.

5. A process as in any of claims 1–4 wherein the bromination catalyst consists essentially of $FeBr_3$ and/or $FeCl_3$, and wherein the benzoyl halide is benzoyl chloride.

6. A process as in any of claims 1–4 wherein the benzoyl halide is benzoyl chloride, and wherein the temperature in B) is in the range of from about 5° C. to about 25° C.

7. A process as in any of claims 1–4 wherein the bromination catalyst consists essentially of $FeBr_3$ and/or $FeCl_3$, wherein the benzoyl halide is benzoyl chloride, and wherein the temperature in B) is in the range of from about 5° C. to about 25° C.

8. A process as in any of claims 1–4 the bromination catalyst consists essentially of $FeBr_3$ and/or $FeCl_3$, wherein the benzoyl halide is benzoyl chloride, and wherein the temperature is in the range of from about 7° C. to about 15° C.

9. A process which comprises
    A) forming a reaction mixture initially comprised of bromine chloride, finely-divided iron, and benzoyl halide; and
    B) maintaining the reaction mixture formed in A) at one or more temperatures above 0° C., but not greater than 30° C., such that meta-bromobenzoyl halide is formed.

10. A process as in claim 9 wherein bromine chloride in the reaction mixture of A) is formed in situ.

11. A process as in claim 9 or 10 wherein the benzoyl halide is benzoyl chloride, and wherein the temperature in B) is in the range of from about 5° C. to about 25° C.

12. A process as in claim 9 or 10 wherein the benzoyl halide is benzoyl chloride, and wherein the temperature in B) is in the range of from about 7° C. to about 15° C.

13. A process which comprises contacting gaseous chlorine with a mixture initially comprised of bromine, finely-divided iron, and a benzoyl halide, and maintaining the temperature of the resultant mixture at one or more temperatures above 0° C., but not greater than 30° C., such that meta-bromobenzoyl halide is formed.

14. A process as in claim 13 wherein the gaseous chlorine is sparged into said mixtures.

15. A process as in claim 13 or 14 wherein the benzoyl halide is benzoyl chloride, and wherein said temperature is in the range of from about 5° C. to about 25° C.

16. A process as in claim 13 or 14 wherein the benzoyl halide is benzoyl chloride, and wherein said temperature is in the range of from about 7° C. to about 15° C.

\* \* \* \* \*